United States Patent [19]
Eckhouse et al.

[11] Patent Number: 5,885,273
[45] Date of Patent: *Mar. 23, 1999

[54] METHOD FOR DEPILATION USING PULSED ELECTROMAGNETIC RADIATION

[75] Inventors: Shimon Eckhouse, Haifa, Israel; Hillel Bachrach, Needham, Mass.

[73] Assignee: ESC Medical Systems, Ltd., Yokneam, Israel

[ * ] Notice: The term of this patent shall not extend beyond the expiration date of Pat. No. 5,683,380.

[21] Appl. No.: 605,321

[22] Filed: Feb. 9, 1996

Related U.S. Application Data

[63] Continuation-in-part of Ser. No. 412,519, Mar. 29, 1995, Pat. No. 5,683,380.

[51] Int. Cl.⁶ ............................................... A61N 5/06
[52] U.S. Cl. ................................. 606/9; 606/2; 606/10; 606/13
[58] Field of Search ........................... 606/2, 3, 9, 10–14

[56] References Cited

U.S. PATENT DOCUMENTS

| | | |
|---|---|---|
| 3,538,919 | 11/1970 | Meyer . |
| 3,693,623 | 9/1972 | Harte . |
| 3,834,391 | 9/1974 | Block . |
| 4,388,924 | 6/1983 | Weissman . |
| 4,617,926 | 10/1986 | Sutton . |
| 5,226,907 | 7/1993 | Tankovich . |
| 5,405,368 | 4/1995 | Eckhouse . |
| 5,595,568 | 1/1997 | Anderson . |
| 5,606,798 | 3/1997 | Kelman ................................. 30/41.6 |

*Primary Examiner*—David M. Shay
*Attorney, Agent, or Firm*—Richard I. Samuel; Theresa A. O'Rourke; Friedman Siegelbaum LLP

[57] ABSTRACT

A method and apparatus for removing hair is disclosed. The method includes the step of producing a plurality of pulses of incoherent electromagnetic energy. The delay between pulses is in the range of 0.1 msec to 100 msec. The incoherent electromagnetic energy is then coupled to an area of surface of the tissue that includes more than one hair follicle. One or more filters are used to provide energy having a wavelength selected in accordance with the color of the hair. The method may alternatively include the step of applying a gel on a surface of the tissue to cool the tissue. The energy heats the hairs and hair follicles, without heating the tissue. The apparatus includes a source of pulsed incoherent electromagnetic energy. The source is located within a housing, and a coupler directs the incoherent electromagnetic energy to the surface of the tissue. In an alternative arrangement a gel disposed on the surface of the tissue such that the gel cools the tissue but is not adjacent, and does not cool, the hair follicle.

9 Claims, 4 Drawing Sheets

METHOD FOR DEPILATION USING PULSED ELECTROMAGNETIC RADIATION

RELATED APPLICATION

This application is a continuation-in-part of prior co-pending U.S. application Ser. No. 08/412,519, filed Mar. 29, 1995, entitled "Method and Apparatus For Depilation Using Pulsed Electromagnetic Radiation," which issued on Nov. 4, 1997, as U.S. Pat. No. 5,683,380 and incorporated herein by reference and is a continuation-in-part of co-prior co-pending U.S. application Ser. No. 08/398,542, filed Mar. 6, 1995, entitled "Method And Apparatus For Therapeutic Electromagnetic Treatment," which is, in turn, a divisional application of U.S. application Ser. No. 07/964,210 which was filed Oct. 20, 1992, entitled "Method And Apparatus For Therapeutic Electromagnetic Treatment," which issued on Apr. 11, 1995, as U.S. Pat. No. 5,405,368.

FIELD OF THE INVENTION

The invention relates generally to devices and methods for removing hair, and more particularly to such devices and methods that utilize electromagnetic energy to kill hair follicles.

BACKGROUND OF THE INVENTION

Hair can be removed permanently for cosmetic reasons by various methods, for example by heating the hair and the hair follicle to a high enough temperature that results in their coagulation. It is known that blood is coagulated when heated to temperatures of the order of 70° C. Similarly, heating of the epidermis, the hair and the hair follicle to temperatures of the same order of magnitude will also cause their coagulation and will result in permanent removal of the hair.

One common method of hair removal, often called electrolysis, is based on the use of "electric needles" that are applied to each individual hair. An electrical current is applied to each hair through the needle. The current heats the hair, causes its carbonization and also causes coagulation of the tissue next to the hair and some coagulation of the micro-vessels that feed the hair follicle.

While the electrical needle method can remove hair permanently or long term, its use is practically limited because the treatment is painful and the procedure is generally tedious and lengthy.

Light can also be used effectively to remove hair. For example, other prior art methods of hair removal involve the application of pulsed light, generally from coherent sources such as lasers. R. A. Harte, et al., in U.S. Pat. No. 3,693,623, and C. Block, in U.S. Pat. No. 3,834,391, teach to remove hair by coagulating single hair with a light coupled to the individual hair by an optical fiber at the immediate vicinity of the hair. Similarly, R. G. Meyer, in U.S. Pat. No. 3,538, 919, removes hair on a hair by hair basis using energy from a pulsed laser. Similar inventions using small fibers are described in U.S. Pat. No. 4,388,924 to H. Weissman, et al. and U.S. Pat. No. 4,617,926 to A. Sutton. Each of these teach to remove hair one hair at a time, and are thus slow and tedious.

U.S. Pat. No. 5,226,907, to N. Tankovich, describes a hair removal method based on the use of a material that coats the hair and hair follicle. The coating material enhances absorption of energy by the follicles, either by matching the frequency of a light source to the absorption frequency of the material, or by photochemical reaction. In either case the light source is a laser. One deficiency of such a method and apparatus is that lasers can be expensive and subject to stringent regulations. Additionally, the coating material must be applied only to the hair follicles, to insure proper hair removal and to prevent damage of other tissue.

Light (electromagnetic) energy used to remove hair must have a fluence such that sufficient energy will be absorbed by the hair and the hair follicle to raise the temperature to the desired value. However, if the light is applied to the surface of the skin other than at the precise location of a hair follicle, the light will also heat the skin to coagulation temperature and induce a burn in the skin.

Accordingly, it is desirable to be able to effectively heat multiple follicles, without burning the surrounding skin. Such a method and apparatus should be able to remove more than one hair at a time, and preferably over a wide area of skin, for example at least two square centimeters. Additionally, the method and apparatus should be capable of using incoherent light.

It is also desirable to provide the light at a frequency selected in accordance with the color of the hair, to take advantage of the absorption frequencies of different colors of hair. Also, it is desirable to provide a delay between pulses that allows the surrounding tissue to cool, but avoids having the hair follicle cool.

SUMMARY OF THE PRESENT INVENTION

In accordance with one aspect of the invention, a method of removing hair from an area of tissue includes producing a plurality of pulses of incoherent electromagnetic energy. The energy is filtered in accordance with the color of the hair being removed. The incoherent electromagnetic energy is then coupled to an area of the surface of the tissue that includes more than one hair follicle.

Additionally, in one alternative embodiment the energy may, but not necessarily, be produced by pulsing a flashlamp to generate a pulse having delays on the order of 0.1 msec to 100 msec, and an energy fluence on the order of 10 to 100 $J/cm^2$. The energy can be coupled through a window in a housing in which the flashlamp is located, by reflecting the energy to the tissue through the window and through a gel located on a surface of the tissue. The window may be brought into contact with the gel. In other alternative embodiments the angular divergence of the electromagnetic energy is controlled, and thus the depth of penetration into the tissue, and the coupling to the hair and to the hair follicles, is also controlled. In another alternative embodiment each step of the method is repeated, but at least two angular divergences are used, thus obtaining at least two depths of penetration.

In other alternative embodiments electromagnetic energy is filtered. Specifically, in one embodiment the electromagnetic energy is filtered according to the pigmentation level of the tissue to be treated, or according to the color of the hair being removed. In another alternative energy that has a wavelength of less than 500 nm or 600 nm and greater than 1300 nm is filtered. Some or all of such energy can be filtered.

In yet another alternative embodiment the pulse produced has a width of less than 200 msec. In one embodiment the surface area of the energy at the tissue is at least two square centimeters.

According to an alternative embodiment the source is a flashlamp and a pulse generating circuit that generates pulses of energy that have an energy fluence on the order of 10 to 100 $J/cm^2$. The coupler can include a transparent window and the housing a reflective interior, wherein the energy is reflected to the window. A gel is disposed on the surface of the tissue and the window is in contact with the gel, to couple the energy through the window and gel to the surface of the tissue. In another alternative embodiment the energy provided by the coupler has a range of angular divergences.

BRIEF DESCRIPTION OF THE DRAWINGS

For a better understanding of the invention, reference is made to the accompanying drawings, in which like numerals designate corresponding elements or sections throughout, and in which.

DETAILED DESCRIPTION OF THE PREFERRED EMBODIMENTS

Figure 1:
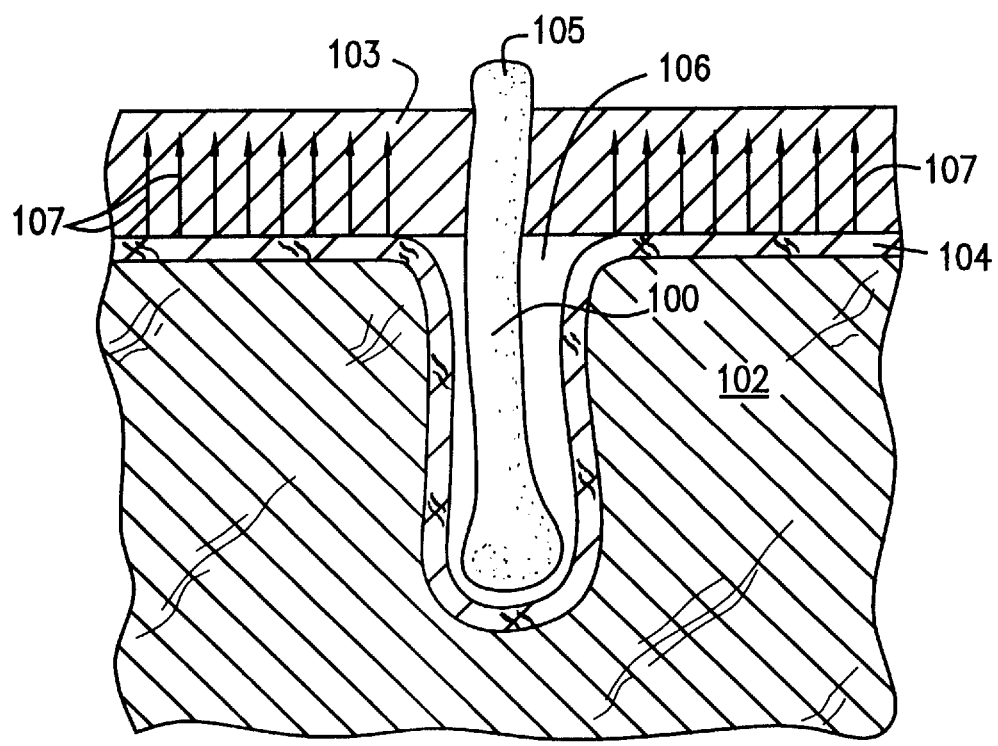
FIG. 1 is a schematic drawing of a cross section of a hair follicle in the dermis and a gel applied to the epidermis in accordance with the present invention.

Before explaining at least one embodiment of the invention in detail it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Generally, in the present invention, hair is removed by exposing the "hairy" area to intense, wide area, pulsed electromagnetic (light) energy. The energy heats the hair and coagulates the tissue around the hair and follicle without damaging the healthy skin.

An optically transparent water based gel may be applied to the skin prior to treatment. As used herein gel means a viscous fluid that is preferably, but not necessarily water based. The gel is used to cool the epidermis which is the primary location of light absorption by tissue, due to the melanin content of the epidermis. The gel is applied so as not to penetrate into the cavity generated by the hair follicle, and thus does not cool the hair and the hair follicle. As a result the energy is selectively applied to coagulate the hair without damaging the skin.

A polychromatic light source, such as a high intensity pulsed flashlamp, is an example of a source suitable for the purposes described herein. One advantage of a polychromatic source such as a flashlamp is that energy having a wavelength in the range of 550 to 630 nm is heavily absorbed in blood and can be used to coagulate the vessel that feeds the hair. Additionally, longer wavelengths, in the range of 600 to 1100 nm have a very good penetration into non-pigmented skin. This wavelength range can be used to couple to the melanin of the hair. The higher pigmentation of the hair and the hair follicle can enhance the absorption of energy by the hair.

Flashlamps also have the advantage of being able to illuminate a large area, thus minimizing the treatment time. The flashlamp combined with a proper reflector can deliver the required fluences to areas on the order of a few square centimeters in a single application. However, other light sources, such as pulsed lasers can be used as well.

Referring now to FIG. 1, a schematic drawing of a cross section of a hair follicle 100 in a dermis 102 is shown. As may be seen in FIG. 1, a gel 103 is applied to an epidermis 104. In the present invention, water based transparent gel 103 is applied to a large section of the skin that is covered by hair, such as hair 105. Gel 103 is applied to epidermis 104 and creates a thin layer on top of epidermis 104. This layer is closely coupled to epidermis 104 and acts as a heat sink that cools epidermis 104 when light (electromagnetic energy) is applied to the area. As may also be seen in FIG. 1, gel 103 does not penetrate into a cavity 106 formed by hair follicle 100 due to its surface tension properties and the fact that the hair is naturally covered by a thin layer of fatty material which makes it hydrophobic. The much higher heat diffusivity of gel 103 compared to that of air which fills cavity 106 enables fast cooling of epidermis 104, represented by arrows 107, while hair 105 is cooled at a much slower rate.

The cooling time—$\delta t$ of an object that has typical dimensions d and diffusivity—$\alpha$ can be written as:

$$\delta t \approx d^2/16\alpha$$

The epidermis has typical cross dimensions of less than 0.1 mm, which is also the typical diameter of hair. The diffusivity of water is approximately $\alpha = 3 \times 10^{-9}$ m$^2$sec$^{-1}$.

The gel is applied, in the manner shown in FIG. 1, over a wide area. When the gel is so applied the typical cooling time of the hair will be on the order of 200 msec and that of the epidermis will be on the order of 5 msec. This difference in cooling times is due to the fact that the gel does not penetrate into the hair follicles. It is preferable to use a transparent gel since the gel acts only as a cooling agent and should not be heated by the external illumination.

In accordance with the invention, light is applied to the treated area in either a long pulse or in a sequence of pulses separated by a delay. The delay and/or pulse length is preferably controlled by the operator to provide enough heat to remove the hair but not enough heat to damage the skin. For example, the pulse length or delay between the pulses should be more than the cooling time of the gel covered epidermis and less than the cooling time of the hair and follicle. Thus, referring to the above discussion on cooling times, a pulse length of 50 msec if a single pulse is used or a delay of 50 msec between the pulses if a pulse sequence is used are appropriate values.

The spectrum of the light source may be selected with reference to the absorption by the skin, by the hair and by the blood vessels feeding the hair. For example, the hair follicle has a typical depth of 1 to 2 mm. It is preferable, therefore, to use a light wavelength range that can penetrate into this depth without very high attenuation.

Figure 2:
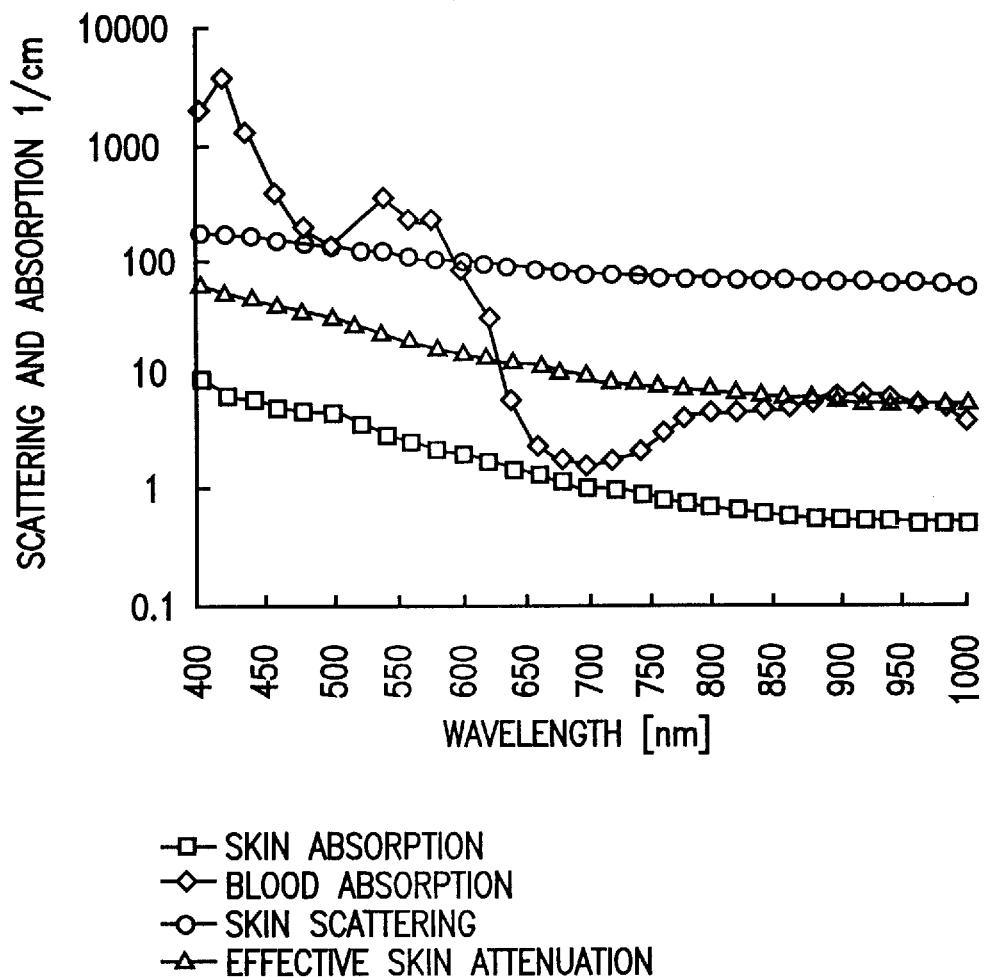
FIG. 2 is a graph showing the optical properties of the skin.

FIG. 2 is a graph showing the scattering, absorption and effective attenuation coefficients in fair skin dermis and the absorption coefficient of blood in the 400 to 1000 nm range. Because a wide area is illuminated, rather than a single hair, it is preferable to use a wavelength range that penetrates into the skin without being highly attenuated. The skin attenuation coefficient controls the depth of penetration of light into the skin. As may be seen in FIG. 2 wavelengths that are longer than 550 nm will be more effective to penetrate deep enough into the skin. Shorter wavelengths are less desirable because they will be highly attenuated before reaching the lower parts of the hair follicles.

Wavelengths significantly longer than 1,000 nm are also less effective due to high absorption of infrared in water which constitutes more than 70% of skin. Wide area photo thermal hair removal of the present invention preferably uses light that can penetrate deep into the skin, since light is coupled to the hair and the hair follicles only after it penetrates through the skin. Most of the spectrum of light at wavelengths longer than 1,300 nm is heavily absorbed in water and will be less useful because it does not penetrate very deep into the skin. For example, $CO_2$ laser radiation in the 10,000 nm range penetrates only a few tens of microns into the skin.

Figure 3:
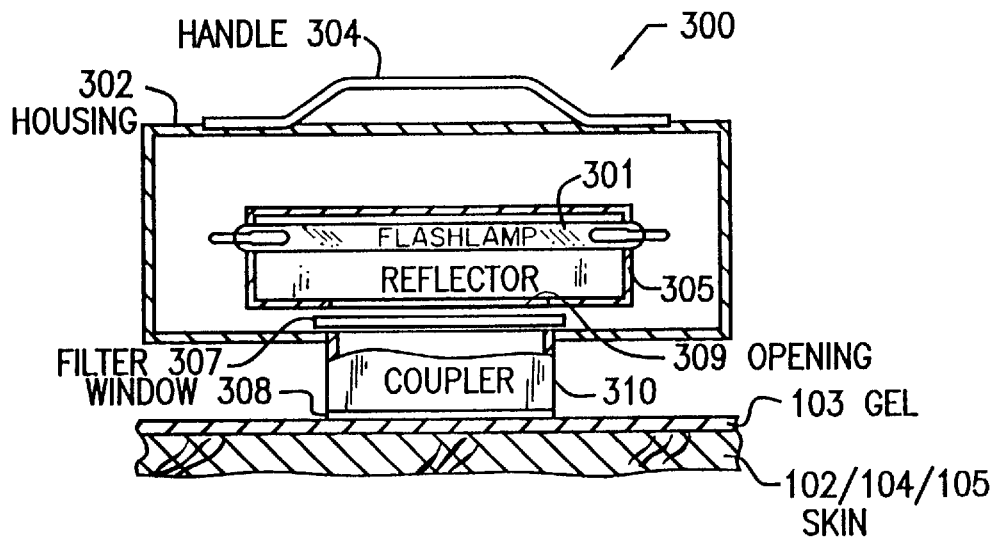
FIG. 3 is a side view of a hair removal apparatus constructed in accordance with the present invention.
Figure 4:
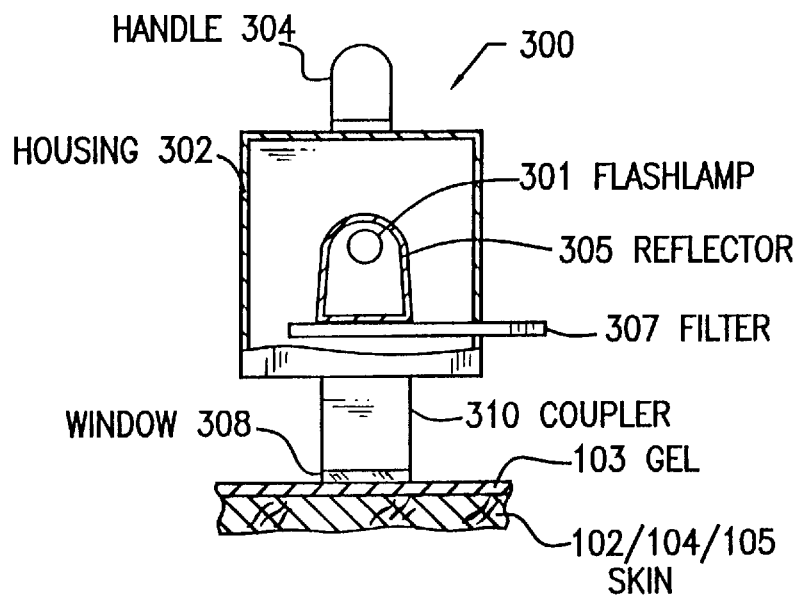
FIG. 4 is a front view of a hair removal apparatus constructed in accordance with the present invention.

Referring now to FIGS. 3 and 4, one preferred embodiment of hair remover 300 includes a flashlamp 301 located in a housing 302 having a handle. The flashlamp is shown adjacent gel 103 and hairy skin 102/104/105. One flashlamp that the inventors have found effective for hair removal is described in detail in co-pending United States Patent Application For Method and Apparatus For Therapeutic Electromagnetic Treatment, Ser. No. 07/964,210, filed Oct. 20, 1992, and incorporated herein by reference. The flashlamp described therein provides a suitable fluence and it illuminates a large area in a single pulse (on the order of 10×50 mm).

Such a flashlamp is driven by a variable pulse width power source. The flashlamp is contained in housing 302 and the light from the flashlamp is directed towards the skin by a reflector 305 that has a high reflectivity.

Also shown in FIGS. 3 and 4 is a filter 307, that is disposed between flashlamp 301 and gel 103. The filter, or in an alternative embodiment, multiple filters, are used to control the spectrum generated by the light source. As used herein filter, or band-pass filter, describes a device that allows electromagnetic energy (light) of certain wavelengths or frequencies to pass. The other wavelengths or frequencies are either partially or wholly removed.

The operator can select the filter according to the skin pigmentation of the person being treated. For the embodiment using a flashlamp, one can take advantage of the spectral range typically generated by such a lamp, which is in the range of 200 to 1300 nm for high pressure xenon flashlamps operated at high current densities (on the order of 1,000 to 5,000 $A/cm^2$). Since hair removal is mainly done for cosmetic reasons and is mostly important for cases of darker hair, the hair itself will absorb light in a wide spectral range in the visible and the near infrared. The shorter wavelengths generated by the flashlamp may be removed since they do not penetrate as deeply into the skin (as can be seen from FIG. 2).

In one embodiment a long pass filter that transmits only wavelengths longer than the cut off wavelength of the filter is used. A cut off wavelength of 600 nm is used in a preferred embodiment when the person being treated has fair skin. A cut off wavelength in the range of 700 to 800 nm is used in the preferred embodiment to treat people with dark skin. According to the invention, the filters may be, for example, dichroic filters or absorbing filters. The desired spectrum can also be achieved by more than one filter or by band-pass filters.

According to one embodiment the filter used is selected based upon the absorption characteristic of the hair. For example, dark hair has a different absorption characteristic than light hair. Thus, the frequency (or wavelength) is tailored to the color of the hair being removed. Dark hair may be best treated by wavelengths of greater than 600 nm, and light hair by wavelengths greater than 500 nm, for example.

Light from flashlamp 301 is coupled to the skin through a transparent window 308 and a coupler 310 (described below). As shown in FIGS. 3 and 4, window 308 is placed on transparent water based gel 103. In use, the operator holds hair remover 300 by handle 304, and places it on the area of skin where treatment is desired (and gel 103 has been applied). Transparent window 308 creates a well defined flat surface on gel 103, through which light enters into gel 103 and into the skin.

The operator selects the pulse and energy fluence parameters on a control unit (not shown). The power and control unit are preferably housed in a separate box and will include power from a capacitor charged to a high voltage by a DC power supply, wherein the capacitor is discharged through the flashlamp. Hair remover 300 can be connected to the power and control unit via a flexible cable that allows easy aiming of the device when aiming it to the treatment area on the patient's skin. Pulse length control can be achieved by using a few pulse forming networks that can generate different pulse widths. Alternatively, an opening 309 may include a solid state opening switch that can stop the discharge at a time preset by the operator, thus controlling the pulse width. These elements of the device are well known and can be easily constructed, or replaced by similar elements, as one skilled in the art will know.

After the parameters have been selected, the operator fires the unit by pressing a switch that can be located in a variety of locations.

A total fluence on the order of 10 to 100 $J/cm^2$ will successfully remove the hair. This fluence can be determined from the requirement of reaching a high enough temperature of the hair and hair follicle, and considering the penetration of light, through the skin and into the hair and hair follicle, absorption of light in the hair and hair follicle, specific heat capacity of the hair and the hair follicle, and the cooling of the hair during the pulse by heat conductivity to the surrounding skin.

Coupler 310 transmits light from flashlamp 301 to gel 103 and to the skin. The coupler can be comprised of a hollow box with internally reflecting walls that act as a light guide for the light generated by flashlamp 301, to transmit the light (electromagnetic energy) to the skin. Coupler 310 may alternatively be made from other material, for example, a solid transparent material such as glass or acrylic in which light reflection from the walls is achieved by using total internal reflection on the side walls.

Coupler 310 is used, in one alternative embodiment, to control the angular distribution of the light rays impinging on the skin. Light rays will hit the hair or the hair follicle predominantly when they are travelling in a direction perpendicular to the plane of the skin. A distribution of light rays that has a relatively wide angular divergence when treating shallow hair is desirable to direct a large portion of the energy to the hairs and follicles. Conversely, a narrow divergence is preferable when deep penetration is desired.

In one embodiment both shallow and deep penetration is obtained by using a two stage treatment process. A narrow divergence beam is used first to treat the deeper hair follicles, while a high divergence beam is used to treat the top of the hair follicles.

Figures 5, 6:
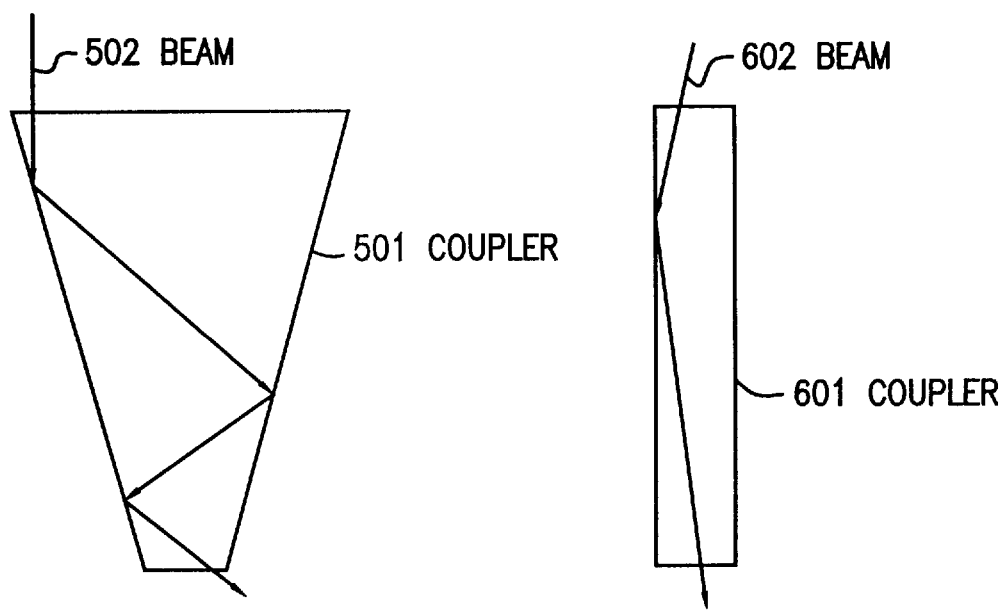
FIG. 5 is a divergent coupler such as one used in the present invention.
FIG. 6 is a non-divergent coupler such as one used in the present invention.

FIG. 5 shows a coupler 501 having an exit beam with a greater angular divergence than that of the entrance beam. As shown in FIG. 5, a beam 502 enters coupler 501 at a small angle, relative to the axis of coupler 501. When beam 502 exits coupler 501 the angle, relative to the axis, is much greater. The tapered shape of coupler 501 enhances this divergence.

FIG. 6 shows a straight coupler 601, that maintains the angular distribution of the rays of light that enter into it. A beam 602 is shown entering and exiting coupler 601 with the same angle, relative to the axis of coupler 601. Alternate use of both couplers 501 and 601 can achieve the narrow and deep penetration discussed above. Alternatively, the user can select the type of coupler according to the depth of hair being treated.

Clinical tests have been performed on hair on the legs of a few patients. Hair was removed for at least two months without observing any hair growing back on the exposed areas during this period. The experiments were performed with high fluences, i.e., up to 45 J/cm$^2$ in each exposure. The spectrum used covered the range of 570 to 1100 nm and the fluence was supplied in a triple pulse with delays of 50 to 100 msec between pulses. The pulse sequence enabled hair removal with minimum pain and no damage to the skin. The transparent gel that was used in these experiments was a water based ultrasound gel, such as that commonly available.

In an alternative embodiment the delay between pulses is on the order of 10 to 100 msec between the pulses, or preferably in the range of 0.1 to 100 msec between pulses. The inventors have found that pulse delays in this range are particularly effective.

Thus, it should be apparent that there has been provided in accordance with the present invention a flashlamp and coupler that fully satisfy the objectives and advantages set forth above. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claim is:

1. A method of removing hair from an area of tissue that includes a plurality of hair follicles; each of said hair follicles having generated a cavity; said method including:

applying a viscous gel to said area of tissue to cool said area of tissue; said viscous gel being applied so as not to penetrate into said cavities, thus not cooling said follicles;

providing a plurality of pulses of electromagnetic energy having one or more wavelengths to which said viscous gel is transparent; and applying said plurality of pulses of electromagnetic energy to said area of said tissue through said viscous gel.

2. The method of claim 1, in which the area of the energy at the tissue is at least two square centimeters.

3. The method of claim 1, in which the step of providing a plurality of pulses includes providing a delay in the range of 0.1 to 100 msec between the pulses.

4. The method of claim 2, wherein the step of providing includes the step of providing at least one pulse having a width of less than 200 msec.

5. The method of claim 3, wherein the step of providing comprises the step of pulsing a flashlamp to generate a pulse having an energy fluence in the range of 10 to 100 J/cm$^2$.

6. The method of claim 5, wherein the flashlamp is located in a housing that includes a transparent window and wherein the step of applying said plurality of pulses includes the steps of reflecting the energy to the tissue, through the window and through the viscous gel located on the surface of the tissue.

7. The method of claim 6, wherein the step of applying said plurality of pulses further includes bringing the window into contact with the viscous gel.

8. The method of claim 7, wherein the step of applying said plurality of pulses includes controlling the angular divergence of the electromagnetic energy, whereby a depth of penetration into the tissue, and the application to the hair and to the hair follicles, is controlled.

9. The method of claim 8, wherein each step of the method is repeated at least twice, and wherein at least two angular divergences are used, whereby at least two depths of penetration are obtained.

* * * * *